US008480713B2

(12) United States Patent
Rezach

(10) Patent No.: US 8,480,713 B2
(45) Date of Patent: Jul. 9, 2013

(54) ADJUSTABLE SPINAL CONNECTOR ASSEMBLY

(75) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 368 days.

(21) Appl. No.: 12/845,156

(22) Filed: Jul. 28, 2010

(65) Prior Publication Data

US 2012/0029566 A1 Feb. 2, 2012

(51) Int. Cl.
*A61B 17/70* (2006.01)

(52) U.S. Cl.
USPC ............................ 606/250; 606/246; 606/251

(58) Field of Classification Search
USPC .......................................... 606/246–278, 66
See application file for complete search history.

(56) References Cited

U.S. PATENT DOCUMENTS

| 5,261,909 A | 11/1993 | Sutterlin et al. | |
|---|---|---|---|
| 5,549,608 A * | 8/1996 | Errico et al. | 606/264 |
| 5,782,833 A * | 7/1998 | Haider | 606/266 |
| 6,030,388 A * | 2/2000 | Yoshimi et al. | 606/278 |
| 6,187,005 B1 * | 2/2001 | Brace et al. | 606/264 |
| 6,471,703 B1 | 10/2002 | Ashman | |
| 6,485,491 B1 * | 11/2002 | Farris et al. | 606/250 |
| 7,022,122 B2 * | 4/2006 | Amrein et al. | 606/266 |
| 7,575,587 B2 * | 8/2009 | Rezach et al. | 606/278 |
| 7,678,112 B2 * | 3/2010 | Rezach | 606/60 |
| 7,753,940 B2 | 7/2010 | Veldman et al. | |
| 7,819,902 B2 * | 10/2010 | Abdelgany et al. | 606/267 |
| 7,850,715 B2 * | 12/2010 | Banouskou et al. | 606/246 |
| 2002/0173789 A1 * | 11/2002 | Howland | 606/61 |
| 2004/0006342 A1 * | 1/2004 | Altarac et al. | 606/61 |
| 2005/0070901 A1 * | 3/2005 | David | 606/61 |
| 2005/0113830 A1 * | 5/2005 | Rezach et al. | 606/60 |
| 2005/0113835 A1 | 5/2005 | Ashman | |
| 2005/0273167 A1 | 12/2005 | Triplett et al. | |
| 2006/0247628 A1 * | 11/2006 | Rawlins et al. | 606/61 |
| 2007/0293861 A1 * | 12/2007 | Rezach et al. | 606/61 |
| 2008/0114359 A1 * | 5/2008 | Murner et al. | 606/66 |
| 2010/0094343 A1 * | 4/2010 | Pham et al. | 606/246 |

* cited by examiner

*Primary Examiner* — Eduardo C Robert
*Assistant Examiner* — James Palmer

(57) ABSTRACT

A spinal connector assembly including a connector body defining first and second passages arranged transverse to one another and configured to receive respective portions of an implant and an elongate rod. A collet receives a portion of the implant therein and extends through the first passage with an upper portion extending axially beyond an upper side of the connector body and a lower portion extending axially beyond a lower side of the connector body. A washer is positioned annularly about the lower portion of the collet and beneath the connector body with a top side of the washer facing a lower side of the connector body and with one of the top and lower sides defining a convex surface and the other defining a concave surface. A lock member is engaged with the upper portion of the collet and exerts an upward force thereon to pull the collet and the washer in an upward direction to draw the convex and concave surfaces into compressed engagement with one another, and the upward force also drawing an outer surface of the collet against an inner engagement surface to inwardly displace a portion of the collet into clamped engagement with the implant member.

29 Claims, 9 Drawing Sheets

ADJUSTABLE SPINAL CONNECTOR ASSEMBLY

BACKGROUND

Spinal implants can be engaged to or along one or more vertebrae of the spinal column for the treatment of various spinal conditions or abnormalities. Elongate rods are commonly used to stabilize and support portions of the spinal column for treatment, either by fixing the spinal column or by permitting at least some degree of motion of the stabilized motion segments. Bone anchors such as, for example, bone screws are provided to secure the elongate rods to one or more vertebrae at a particular location along the spinal column. In some instances, connectors or other types of coupling devices are used to interconnect the rods with the bone anchors. Current connectors and coupling devices are not particularly easy to use and/or are not sufficiently adjustable to accommodate for variations in the position and/or angular orientation of the bone anchors relative to the elongate rods, and/or are otherwise deficient in operation. Thus, there remains a need in the art for an adjustable spinal connector assembly that provides advantages over existing connector or coupler devices.

SUMMARY

The present invention relates generally to a connector assembly, and more particularly but not exclusively relates to an adjustable spinal connector assembly that accommodates for variations in the position and/or angular orientation of a bone anchor relative to an elongate support member.

According to one aspect, a connector assembly is provided including a connector body including a first receiver portion defining a first passage extending therethrough from an upper side to an oppositely facing lower side and arranged along a first axis, and a second receiver portion defining a second passage extending therethrough and arranged along a second axis transverse to the first axis, and the second passage sized to receive a portion of the elongate support member therein. The connector assembly further includes a collet member defining a third passage extending therethrough and sized to receive a proximal portion of the implant member therein, and the collet member extends through the first passage in the connector body and includes an upper proximal portion extending axially beyond the upper side of the connector body and a lower distal portion extending axially beyond the lower side of the connector body, with the collet member configured to pivot within the first passage of the connector body to position the collet member and the implant member at variable angular orientations relative to the first axis. A washer member defining an opening extending therethrough is positioned annularly about the lower distal portion of the collet member and is positioned beneath the first receiver portion of the connector body with a top side of the washer member facing the lower side of the first receiver portion, and one of the top side and the lower side defines a convex surface, and another of the top side and the lower side defines a concave surface facing and generally aligned with the convex surface. A lock member is engaged with the upper proximal portion of the collet member and is positioned adjacent the upper side of the first receiver portion of the connector body. The lock member exerts an upward force onto the collet member to pull the collet member and the washer member in an upward direction which draws the convex and concave surfaces into compressed engagement to thereby lock the washer member and the implant member at a select angular orientation relative to the first receiver portion, and the upward force also drawing an outer surface of the collet member against an inner engagement surface to inwardly displace a portion of the collet member into clamped engagement with the proximal portion of the implant member positioned within the third passage to thereby lock the collet member at a select position along the proximal portion of the implant member.

According to another aspect, a connector assembly is provided including a connector body including a first receiver portion defining a first passage extending therethrough from an upper side to an oppositely facing lower side and arranged along a first axis, and a second receiver portion defining a second passage extending therethrough and arranged along a second axis transverse to the first axis, and the second passage sized to receive a portion of the elongate support member therein. The connector assembly further includes a collet member defining a third passage extending therethrough and sized to receive a proximal portion of the implant member therein, and the collet member extends through the first passage in the connector body and includes an upper proximal portion extending axially beyond the upper side of the connector body and a lower distal portion extending axially beyond the lower side of the connector body, with the collet member configured to pivot within the first passage of the connector body to position the collet member and the implant member at variable angular orientations relative to the first axis. A washer member defining an opening extending therethrough is positioned annularly about the lower distal portion of the collet member and is positioned beneath the first receiver portion of the connector body with a top side of the washer member facing the lower side of the first receiver portion, and the top side of the washer member and the lower side of the first receiver portion together defining a plurality of mating engagement elements that are configured to selectively interdigitate with one another. A lock member is engaged with the upper proximal portion of the collet member and is positioned adjacent the upper side of the first receiver portion of the connector body. The lock member exerts an upward force onto the collet member to pull the collet member and the washer member in an upward direction which draws the mating engagement elements into interdigitating engagement with one another to thereby lock the washer member and the implant member at a select angular orientation relative to the first receiver portion, and the upward force also drawing an outer surface of the collet member against an inner engagement surface to inwardly displace a portion of the collet member into clamped engagement with the proximal portion of the implant member positioned within the third passage to thereby lock the collet member at a select position along the proximal portion of the implant member.

According to a further aspect, a stabilization system to stabilize a bony segment is provided including an elongate support rod, a bone anchor including a bone engaging portion and a proximal post portion, and a connector assembly configured to transversely interconnect the elongate support rod with the bone anchor. The connector assembly includes a connector body including a first receiver portion defining a first passage extending therethrough from an upper side to an oppositely facing lower side and arranged along a first axis, and a second receiver portion defining a second passage extending therethrough and arranged along a second axis transverse to the first axis, and with a portion of the elongate support rod positioned within the second passage. The connector assembly further includes a collet member defining a third passage extending therethrough with the proximal post portion of the bone anchor positioned therein, and the collet member extends through the first passage in the connector body and includes an upper proximal portion extending axially beyond the upper side of the connector body and a lower distal portion extending axially beyond the lower side of the connector body, with the collet member configured to pivot within the first passage of the connector body to position the collet member and the proximal post portion of the bone anchor at variable angular orientations relative to the first axis. A washer member defining an opening extending therethrough is positioned annularly about the lower distal portion of the collet member and is positioned beneath the first receiver portion of the connector body with a top side of the washer member facing the lower side of the first receiver portion, and one of the top side and the lower side defines a convex surface, another of the top side and the lower side defines a concave surface facing and generally aligned with the convex surface, and the convex and concave surfaces together defining a plurality of mating engagement elements that are configured to selectively interdigitate with one another. A lock member is engaged with the upper proximal portion of the collet member and is positioned adjacent the upper side of the first receiver portion of the connector body. The lock member exerts an upward force onto the collet member to pull the collet member and the washer member in an upward direction which draws the mating engagement elements into interdigitating engagement with one another to thereby lock the washer member and the proximal post portion of the bone anchor at a select angular orientation relative to the first receiver portion, and the upward force also drawing an outer surface of the collet member against an inner engagement surface to inwardly displace a portion of the collet member into clamped engagement with the proximal post portion of the bone anchor positioned within the third passage to thereby lock the collet member at a select position along the proximal post portion of the bone anchor.

Further embodiments, forms, features, aspects, benefits, objects and advantages of the spinal connector assembly will become apparent from the detailed description and figures provided herewith.

DESCRIPTION OF THE ILLUSTRATED EMBODIMENTS

Figure 1:
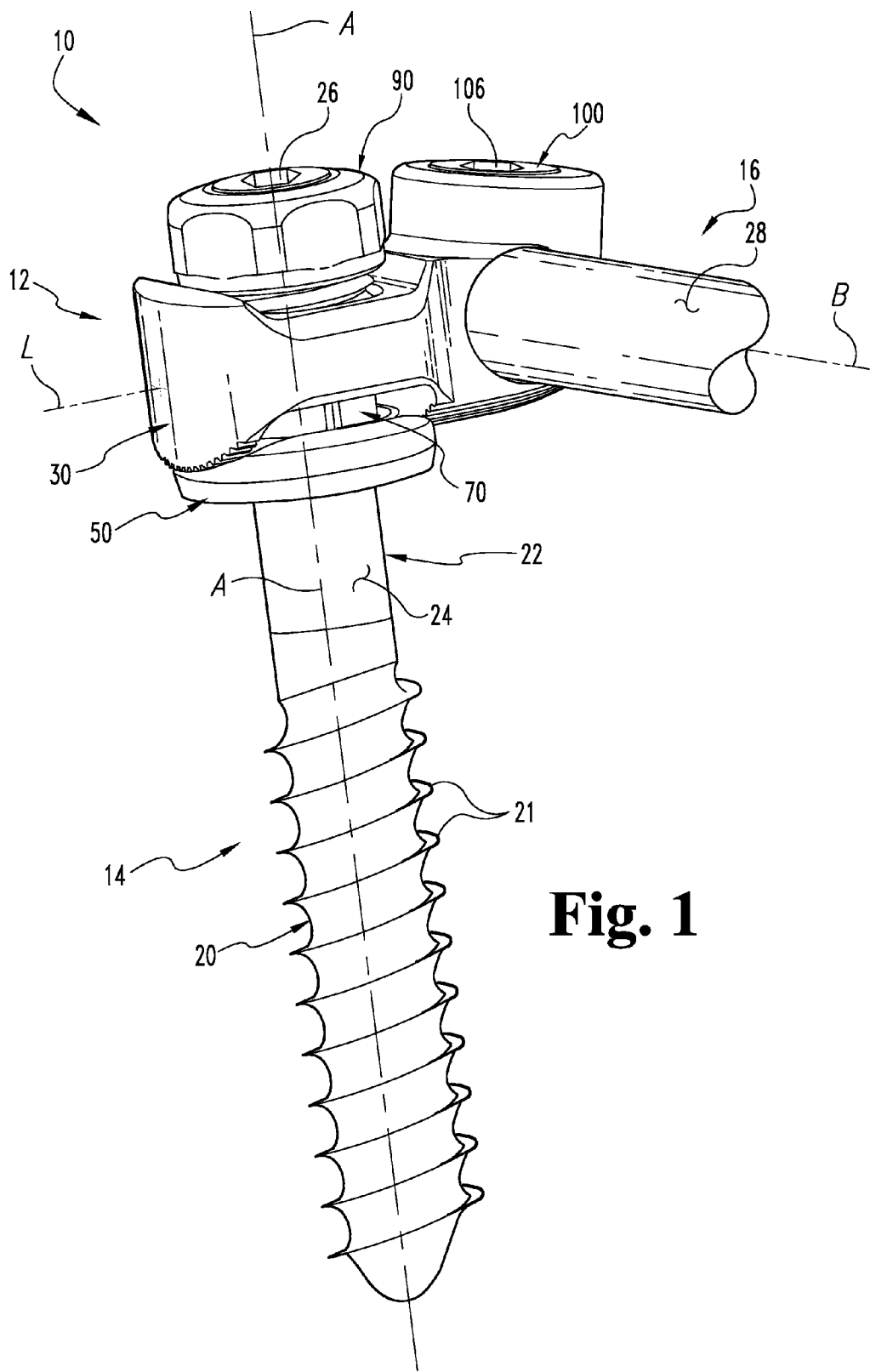
FIG. 1 is a perspective view of a spinal connector assembly according to one form of the present invention.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Figure 2:
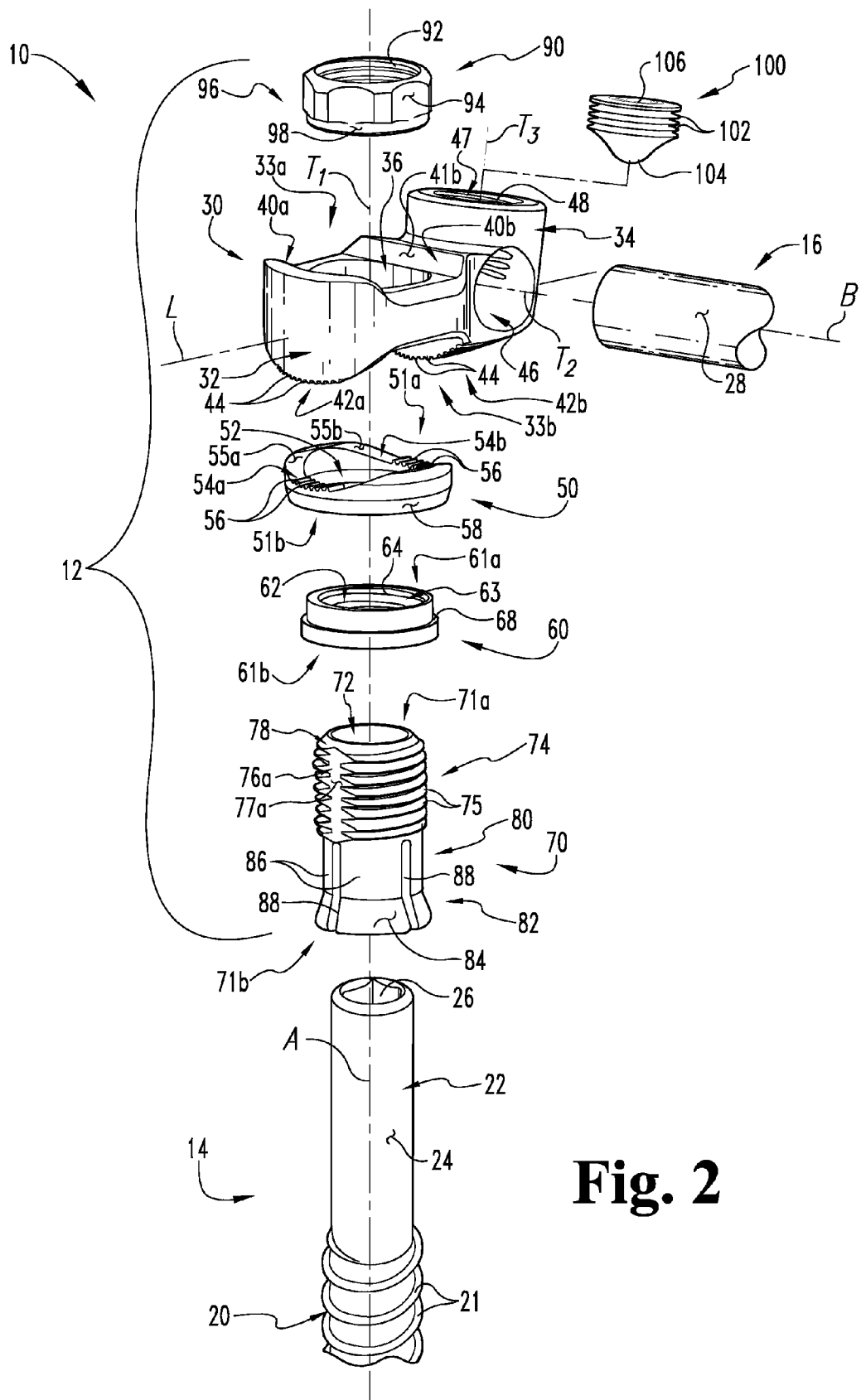
FIG. 2 is an exploded perspective view of the spinal connector assembly illustrated in FIG. 1.

Referring to FIGS. 1 and 2, shown therein is spinal stabilization system 10 according to one form of the present invention. The spinal stabilization system 10 generally includes an adjustable spinal connector assembly 12 extending generally along a longitudinal axis L that is configured to interconnect a bone anchor member 14 extending generally along a bone anchor axis A with an elongate support member 16 extending generally along a support member axis B that is laterally offset from and arranged transverse to the bone anchor axis A. As will be discussed in greater detail below, in the illustrated embodiment, the bone anchor member 14 comprises a bone screw and the elongate support member 16 comprises a spinal rod. However, other types and configurations of the bone anchor member 14 and the elongate support member 16 are also contemplated for use in association with the present invention. Additionally, it should be understood that the connector assembly 12 may be used to interconnect various types and configurations of spinal implants, and is not limited to interconnecting a bone anchor member with an elongate support member. It should also be understood that the connector assembly 12 may be used in fields outside of the spinal field including, for example, in fixation or stabilization systems that are attached to other bony structures including the pelvis, the skull and/or the occiput, long bones, or other bony structures that would occur to those having ordinary skill in the art.

In the illustrated embodiment, the connector assembly 12 generally includes a connector body or housing 30, a washer member or collar 50, a ring member 60, a collet member or sleeve 70, a lock member or nut 90, and a compression member or set screw 100. As will be discussed in greater detail below, the connector body 30 is configured to connect the bone anchor member 14 with the elongate support member 16. Additionally, the washer member 50, the ring member 60, the collet member 70, and the lock member 90 cooperate with the connector body 30 and with one another to lock the connector body 30 at a particular position or height along the transverse axis A of the bone anchor member 14, and to lock the connector body 30 at a particular angular orientation relative to the bone anchor member 14. The compression member 100 further cooperates with the connector body 30 to lock the elongate support member 16 at a particular position along the transverse axis B relative to the connector body 30. The connector assembly 12 thereby serves to lock the elongate support member 16 in a select position and angular orientation relative to the bone anchor member 14. The components and elements of the spinal stabilization system 10 may be formed of various biocompatible materials including, for example, stainless steel, titanium, ceramics, plastics such as PEEK, or any other biocompatible material know to those having ordinary skill in the art.

In the illustrated embodiment, the bone anchor member 14 generally includes a bone engaging portion 20 and a proximal connecting portion 22. In one particular embodiment, the bone anchor member 14 is configured as a bone screw, and more particularly a Schanz-type bone screw where the bone engaging portion 20 is configured as a threaded shank including bone engaging threads 21 adapted for anchoring in bone, and where the proximal connecting portion 22 is configured as a cylindrical-shaped head or post including a substantially circular and smooth outer surface 24 having a generally uniform outer diameter that is substantially equal to the root diameter of the bone engaging threads 21. However, it should be understood that the connecting portion 22 may be provided with other shapes and configurations and may be roughened or textured. The connecting portion 22 is also provided with a tool engaging feature 26 configured for releasable engagement with a driver instrument (not shown) to facilitate driving of the bone anchor member 14 into bone. In the illustrated embodiment, the tool engaging feature 26 comprises a tool receiving recess or print extending axially into the connecting portion 22 from a proximal end thereof, and which is sized and configured to receive a distal end portion of a driver instrument therein. In one embodiment, the tool receiving recess 26 has a hexagonal configuration, although other shapes are also contemplated. It should be understood that other types and configurations of tool engaging features are also contemplated including, for example, a tool engaging projection or stem extending axially from the proximal end of the connecting portion 22. It should also be understood that other types and configurations of bone screws are also contemplated including, for example, bone screws having other thread configurations and/or other types of proximal connecting portions. Additionally, other types and configurations of bone anchor members are also contemplated for use in association with the present invention including, for example, hooks, pins, bolts, clamps, staples, interbody devices, or any other type of bone anchor device know to those having ordinary skill in the art.

In the illustrated embodiment, the elongate support member 16 is configured as a spinal rod including a substantially smooth outer surface 28 defining a circular outer cross section having a substantially uniform outer diameter. However, it should be understood that the elongate support member 16 may be provided with other cross sectional shapes, and the outer surfaces 28 may be roughened (e.g., via knurling or threading) or otherwise textured. It should also be understood that other types and configurations of elongate support members are also contemplated for use in association with the present invention including, for example, bars, elongate plates, wires, tethers, or any other elongate support member know to those having ordinary skill in the art.

Figure 3:
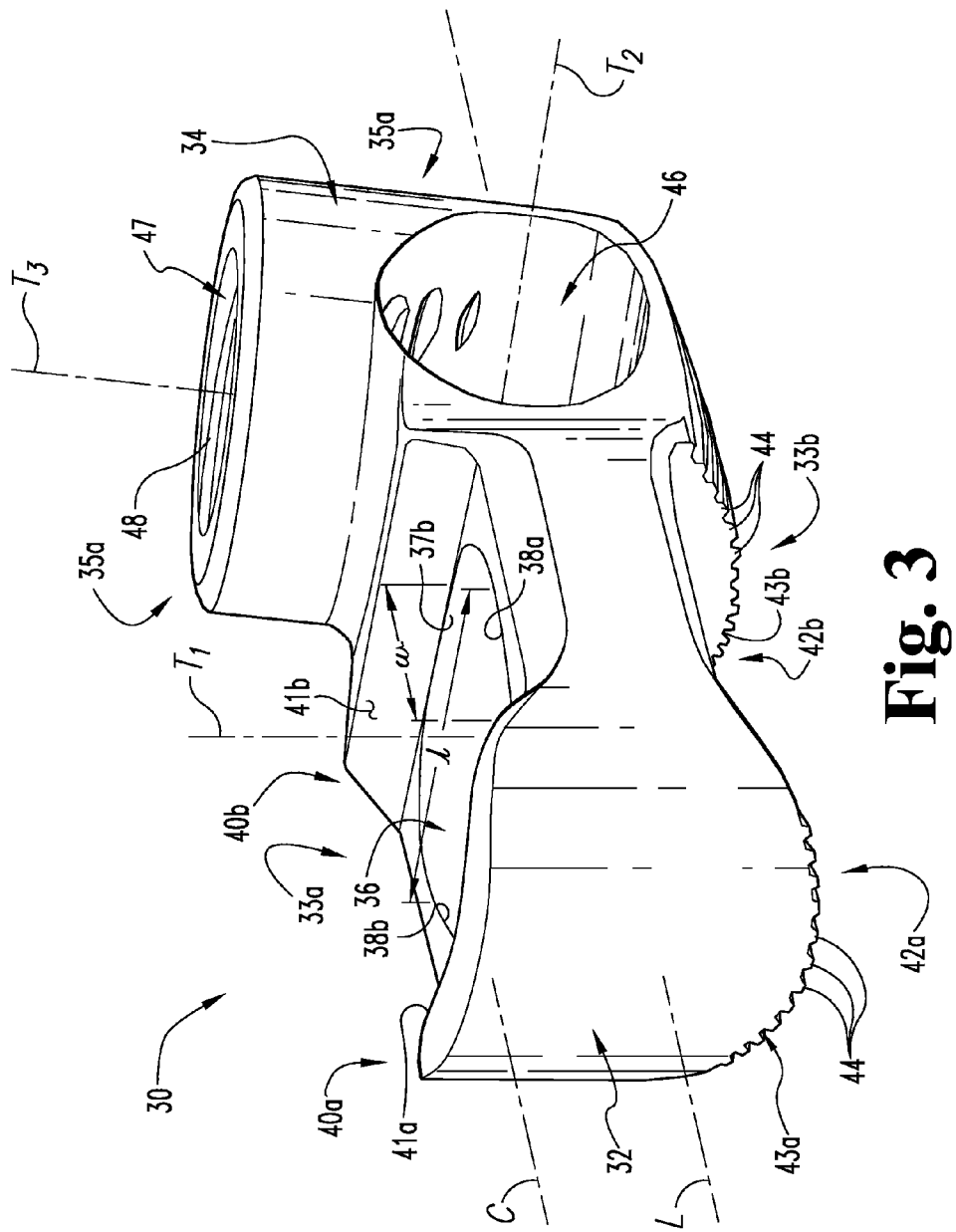
FIG. 3 is a perspective view of a connector body included in the spinal connector assembly illustrated in FIG. 1.

Referring collectively to FIGS. 2 and 3, shown therein are further details associated with the connector body or housing 30. In the illustrated embodiment, the connector body 30 extends generally along a longitudinal axis L and includes a bone anchor or screw receiving portion 32 and a support member or rod receiving portion 34. The screw receiving portion 32 and the rod receiving portion 34 are offset from one another along the longitudinal axis L. In one embodiment, the screw receiving portion 32 and the rod receiving portion 34 are formed integral with one another to provide the connector body 30 as a unitary, single-piece structure wherein the screw receiving portion 32 and the rod receiving portion 34 are non-movable relative to one another. However, other configurations of the connector body 30 are also contemplated wherein the screw receiving portion 32 and the rod receiving portion 34 are formed separately and coupled to one another by a connection mechanism, either in a rigid, non-movable embodiment or in an embodiment wherein the screw receiving portion 32 and the rod receiving portion 34 are movably coupled to one another to allow relative translational movement therebetween generally along or transverse to the longitudinal axis L and/or relative rotational movement therebetween about the longitudinal axis L.

In the illustrated embodiment, the screw receiving portion 32 includes an upper side 33a and an oppositely facing lower side 33b, and also defines a screw receiving passage 36 extending through the screw receiving portion 32 generally along a transverse axis $T_1$ from the upper side 33a to the lower side 33b. In one embodiment, the screw receiving passage 36 is configured as an oblong or elongate slotted passage including generally flat/planar side walls 37a, 37b defining a slot width w extending generally along the longitudinal axis L of the connector body 30, and including end walls 38a, 38b defining a slot length/extending generally perpendicular or normal to the longitudinal axis L. However, other shapes and configurations of the screw receiving passage 36 are also contemplated including, for example, circular shapes or configurations wherein the side walls 37a, 37b and/or the end walls 38a, 38b inwardly taper toward a mid-portion of the passage 36 so as to define one or more protruding portions extending into the passage. In still other embodiments, one or more portions of the side walls 37a, 37b and/or the end walls 38a, 38b may define convex or concave portions and may be at least partially conical shaped or at least partially spherical shaped.

The upper side 33a of the screw receiving portion 32 includes a pair of upper protrusions or lips 40a, 40b arranged on opposite sides of the passage 36 and extending generally along the length l of the passage 36. The upper protrusions 40a, 40b define angled upper surfaces 41a, 41b, respectively, that inwardly taper along the transverse axis $T_1$ toward the passage 36. In the illustrated embodiment, the angled upper surfaces 41a, 41b are substantially flat/planar. However, other configurations are also contemplated, including configurations where the upper surfaces 41a, 41b are provided with a curved or arcuate configuration or a non-tapered configuration. The lower side 33b of the screw receiving portion 32 includes a pair of lower protrusions or rails 42a, 42b arranged on opposite sides of the passage 36 and extending generally along the length l of the passage 36. The lower protrusions 42a, 42b are arranged generally opposite the upper protrusions 40a, 40b and define curved or arcuate lower surfaces 43a, 43b, respectively, each having a curvature extending along the length l of the passage 36 and curving relative to a central axis C that is arranged generally parallel to the longitudinal axis L. In the illustrated embodiment, the curved lower surfaces 43a, 43b each have a convexly curved circular configuration. However, other configurations of the lower surfaces 43a, 43b are also contemplated, including a concave configuration, a curvilinear configuration, or a flat/planar configuration. Additionally, the curved lower surfaces 43a, 43b need not necessarily be circular, but may instead have an elliptical or oval shaped configuration. In the illustrated embodiment, the convexly curved lower surfaces 43a, 43b each define a plurality of engagement elements 44, the purpose of which will be discussed below. In one embodiment, the engagement elements 44 are configured as splines or triangular-shaped teeth 44 extending generally along the longitudinal axis L and across the width of each of the lower protrusions or rails 42a, 42b. However, other shapes and configurations of the splines or teeth 44 are also contemplated. Additionally, in other embodiments, the lower surfaces 43a, 43b may be provided with other types and configurations of engagement elements or may be roughened or otherwise textured. In still other embodiments, the lower surfaces 43a, 43b may be substantially smooth and devoid of any surface projections or surface roughening.

In the illustrated embodiment, the rod receiving portion 34 includes a lateral side 35a and an oppositely facing lateral side 35b, and also defines a rod receiving passage 46 extending through the rod receiving portion 34 generally along a transverse axis $T_2$ from the lateral side 35a to the opposite lateral side 35b. In one embodiment, the transverse axis $T_2$ of the rod receiving passage 46 is laterally offset from and arranged substantially perpendicular or normal to the transverse axis $T_1$ of the screw receiving passage 36. However, other embodiments are also contemplated wherein the transverse axes $T_1$, $T_2$ are arranged substantially in the same plane and/or are arranged at an oblique angle relative to one another. In still other embodiments, the transverse axes $T_1$, $T_2$ may be arranged generally parallel to one another. In the illustrated embodiment, the rod receiving passage 46 has a circular cylindrical shape and has a closed configuration such that the elongate rod member 16 is loaded into the rod receiving passage 46 in a direction along the transverse axis $T_2$. However, other shapes and configurations of the passage 46 are also contemplated including, for example, an oblong or elongate slot-like configuration or an open configuration including an opening extending through an upper, lower or end surface of the rod receiving portion 34 and into communication with the passage 46 so as to provide the passage 46 with a U-shaped or C-shaped configuration to permit top, bottom or lateral side/end loading of the elongate rod member 16 into the rod receiving passage 46 in a direction transverse to the transverse axis $T_2$.

In the illustrated embodiment, the rod receiving portion 34 further defines an opening 47 extending through an outer surface of the rod receiving portion 34 along a transverse axis $T_3$ and into communication with the rod receiving passage 46. As will be discussed in greater detail below, the opening 47 is sized and configured to receive the compression member 100, which in turn is compressed against the elongate rod 16 positioned within the rod receiving passage 46 so as to securely engage the elongate rod 16 to the connector body 30. In one embodiment, the opening 47 defines internal threads 48 configured for threading engagement with external threads formed along the compression member 100. In another embodiment, the transverse axis $T_3$ along which the opening 47 extends is arranged at an oblique angle relative to the transverse axis $T_1$ of the screw receiving passage 36. However, other embodiments are also contemplated where the transverse axis $T_3$ is arranged parallel or perpendicular to the transverse axis $T_1$. Additionally, in the illustrated embodiment, the transverse axis $T_3$ is aligned with and intersects the transverse axis $T_2$ of the rod receiving passage 46. However, other embodiments are also contemplated where the transverse axis $T_3$ is offset from the transverse axis $T_2$ of the rod receiving passage 46.

Figure 4:
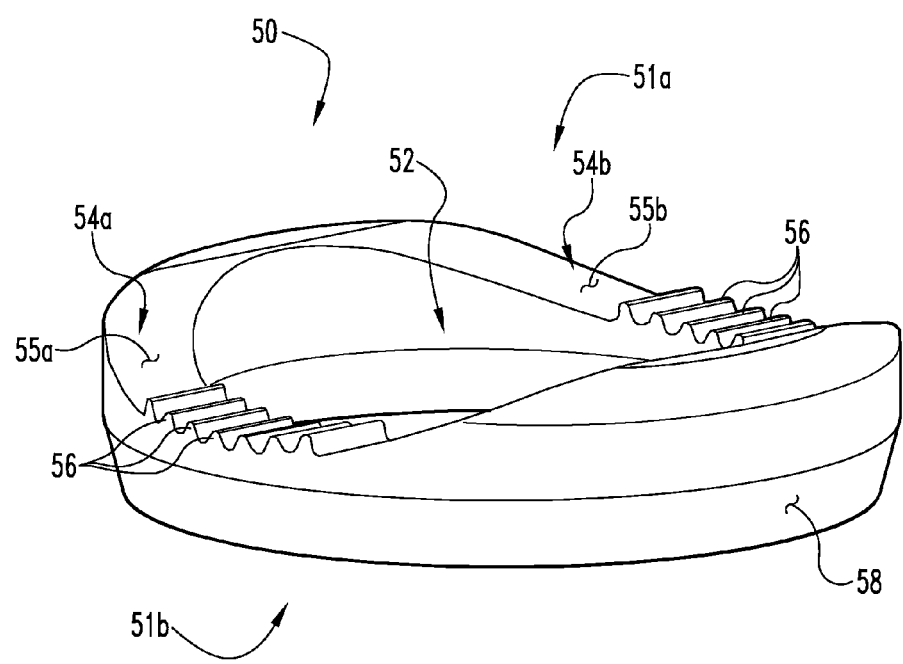
FIG. 4 is a perspective view of a washer member included in the spinal connector assembly illustrated in FIG. 1.
Figure 7:
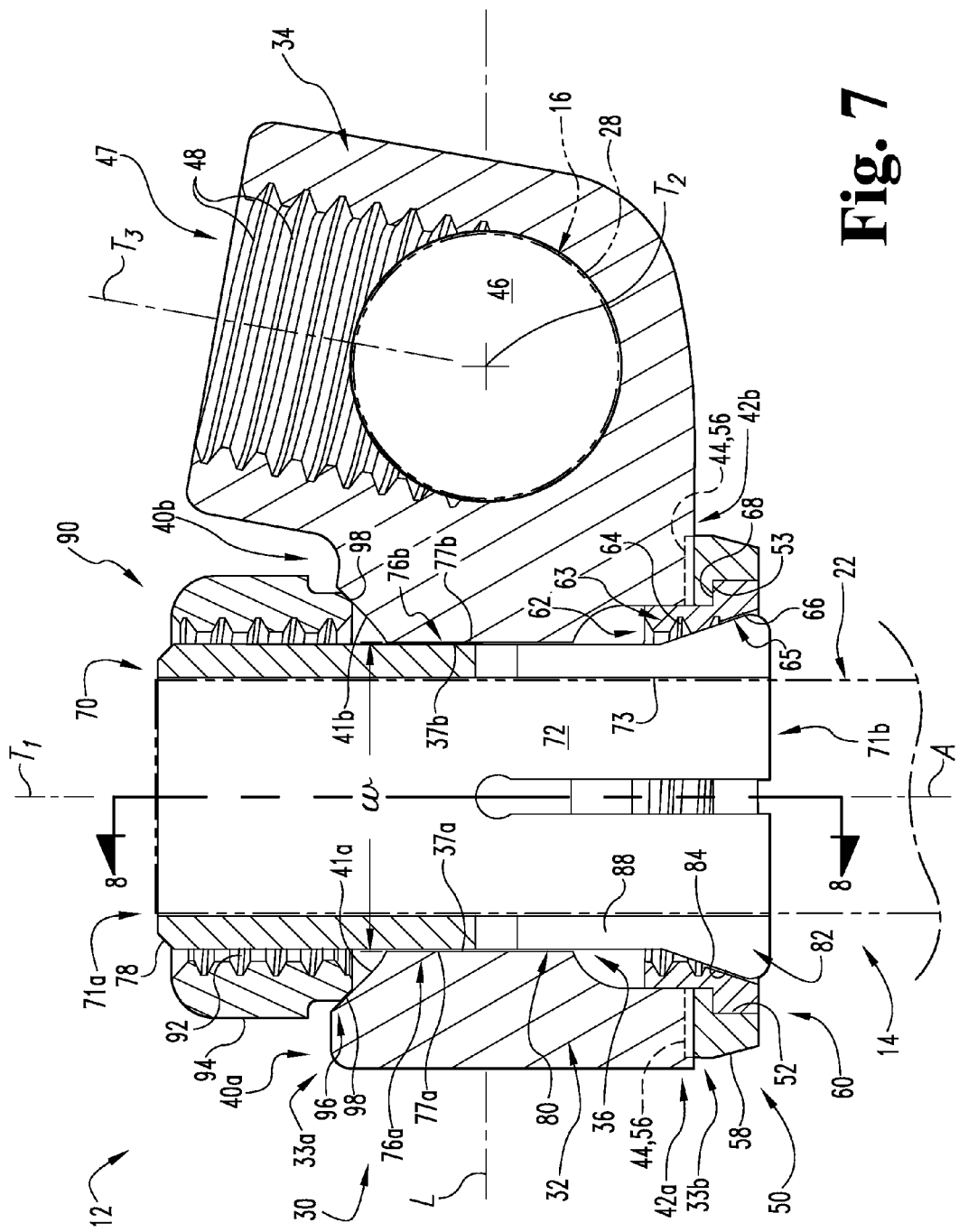
FIG. 7 is a cross sectional elevational view of the spinal connector assembly illustrated in FIG. 1, as taken along the longitudinal axis of the connector body.
Figure 8:
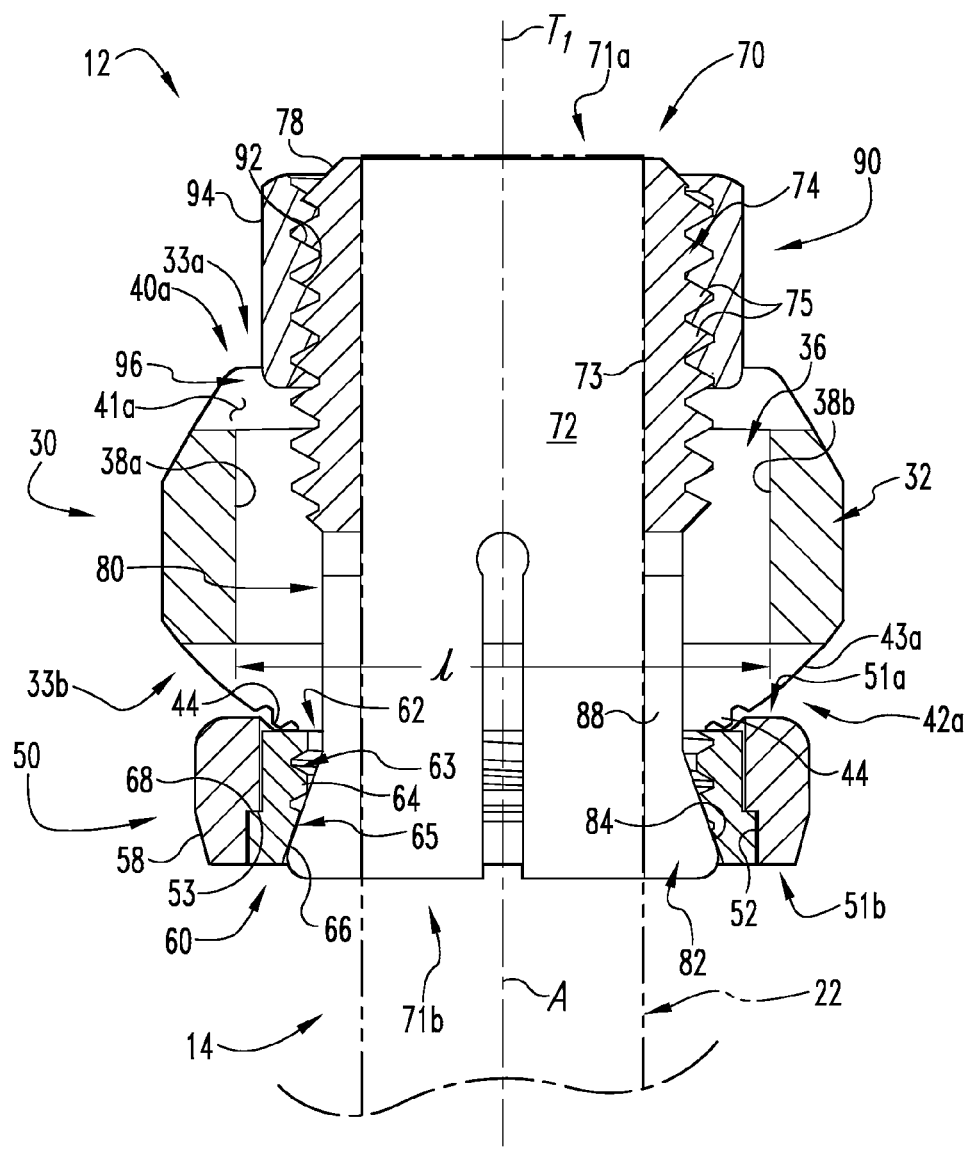
FIG. 8 is a cross sectional elevational view of the spinal connector assembly illustrated in FIG. 7, as taken along line 8-8 of FIG. 7.

Referring collectively to FIGS. 2 and 4, shown therein are further details associated with the washer member or collar 50. In the illustrated embodiment, the washer member 50 has an annular ring-shaped configuration defining a generally circular outer cross section and includes an upper side 51a and an oppositely facing lower side 51b. The washer member 50 further defines an opening 52 extending therethrough from the upper side 51a to the lower side 51b. In one embodiment, the opening 52 has a generally circular inner cross section defining a substantially uniform inner diameter. However, other shapes and configurations of the outer cross section of the washer member 50 and the inner cross section of the opening 52 are also contemplated including, for example, an oblong, elongate, oval or elliptical shape, or a square or rectangular shape. As illustrated in FIGS. 7 and 8, an upper portion of the opening 52 in the washer member 50 adjacent the upper side 51a has an inner cross section that is sized smaller than the inner cross section of a lower portion of the opening 52 adjacent the lower side 51b so as to define an annular shoulder or ledge 53 between the upper and lower portions of the opening 52, the purpose of which will be discussed below.

The upper side 51a of the washer member 50 includes a pair of recessed regions or indentations 54a, 54b arranged on opposite sides of the opening 52. The recessed regions 54a, 54b are arranged generally opposite and are generally aligned with the lower protrusions or rails 42a, 42b defined by the screw receiving portion 32 of the connector body 30 such that the lower protrusions 42a, 42b are received within the recessed regions 54a, 54b when the washer member 50 is positioned adjacent the screw receiving portion 32 of the connector body 30. The recessed regions 54a, 54b define curved or arcuate upper surfaces 55a, 55b, respectively, each having a curvature substantially the same as the curvature of the curved lower surfaces 43a, 43b defined by the lower protrusions of the connector body 30. In the illustrated embodiment, the curved upper surfaces 55a, 55b each have a concave circular configuration. However, other configurations of the upper surfaces 55a, 55b are also contemplated, including a convex configuration, a curvilinear configuration, or a flat/planar configuration. Additionally, it should be understood that the curved upper surfaces 55a, 55b need not necessarily be circular, but may instead have an elliptical or oval shaped configuration. In the illustrated embodiment, the concave upper surfaces 55a, 55b each define a plurality of engagement elements 56. In one embodiment, the engagement elements 56 are configured substantially the same as the engagement elements 44 defined along the curved lower surfaces 43a, 43b of the lower protrusions 42a, 42b of the connector body 30 such that the engagement elements 44, 56 may matingly cooperate or interdigitate with one another. In the illustrated embodiment, the engagement elements 44, 56 are configured as splines or triangular-shaped teeth. However, other shapes and configurations of the interdigitating splines or teeth 44, 56 are also contemplated. In other embodiments, the upper surfaces 55a, 55b may be provided with other types and configurations of engagement elements or may be roughened or otherwise textured. In still other embodiments, the upper surfaces 55a, 55b may be substantially smooth and devoid of any surface projections or surface roughening. The lower portion of the washer member 50 is provided with a conically tapered or rounded outer surface 58 to reduce the risk of damage or trauma to adjacent tissue.

Figure 5:
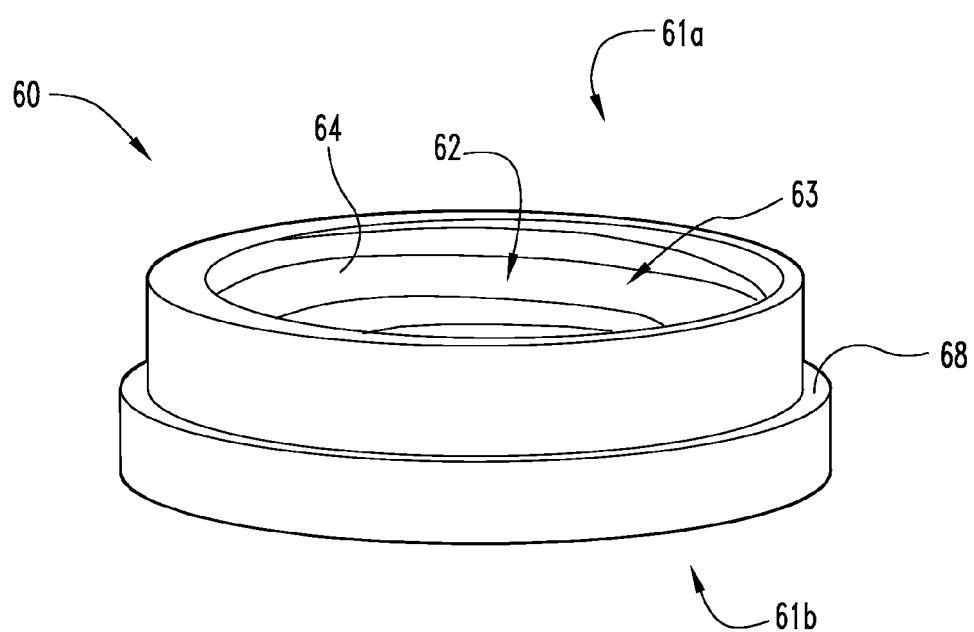
FIG. 5 is a perspective view of a ring member included in the spinal connector assembly illustrated in FIG. 1.

Referring collectively to FIGS. 2 and 5, shown therein are further details associated with the ring member or load transfer member 60. In the illustrated embodiment, the ring member 60 has an annular ring-shaped configuration defining a generally circular outer cross section and includes an upper side 61a and an oppositely facing lower side 61b. However, other shapes and configurations of the ring member 60 are also contemplated. The ring member 60 further defines an aperture 62 extending therethrough from the upper side 61a to the lower side 61b. In the illustrated embodiment, the aperture 62 has a generally circular inner cross section and includes a threaded upper portion 63 extending from the upper side 61a and defining internal threads 64 configured for threading engagement with external threads 75 formed along the threaded upper portion 74 of the collet member 70. Additionally, in the illustrated embodiment, the aperture 62 includes a tapered lower portion 65 defining an angled or tapered inner surface 66 extending from the threaded upper portion 63 to the lower side 61b. In one embodiment, the tapered inner surface 66 has conical shaped configuration. However, other shapes and configurations of the inner surface 66 are also contemplated including, for example, a concave and/or a convex configuration that may define a rounded or spherical shape. As will be discussed in greater detail below, the tapered inner surface 66 of the ring member 60 is configured to contact/abut a tapered outer surface 84 defined by a lower portion 82 of the collet member 70 so as to compress or clamp the collet member 70 about the proximal post portion 22 of the bone anchor 14 to thereby secure the bone anchor 12 to the connector body 30.

In the illustrated embodiment, an upper portion of the ring member 60 has an outer cross section that is sized smaller than a lower portion of the ring member 60 so as to define an annular shoulder or ledge 68 between the upper and lower portions. As illustrated in FIGS. 7 and 8, the upper and lower portions of the ring member 60 are sized in relatively close tolerance with the upper and lower portions of the opening 52 in the washer member 50 to provide a relatively close fit between the ring member 60 and the washer member 50. When the upper and lower portions of the ring member 60 are positioned within the upper and lower portions of the opening 52 in the washer member 50, the annular shoulder 53 of the washer member 50 contacts/abuts against the annular shoulder 68 of the ring member 60 to thereby permit the transfer of axial forces from the washer member 50 to the ring member 60, the purpose of which will be discussed in greater detail below. Additionally, although the washer member 50 and the ring member 60 are illustrated and described as being provided as separate pieces, in other embodiments, the washer member 50 and the ring member 60 may be formed integral with one another so as to define a unitary, single-piece structure.

Figure 6:
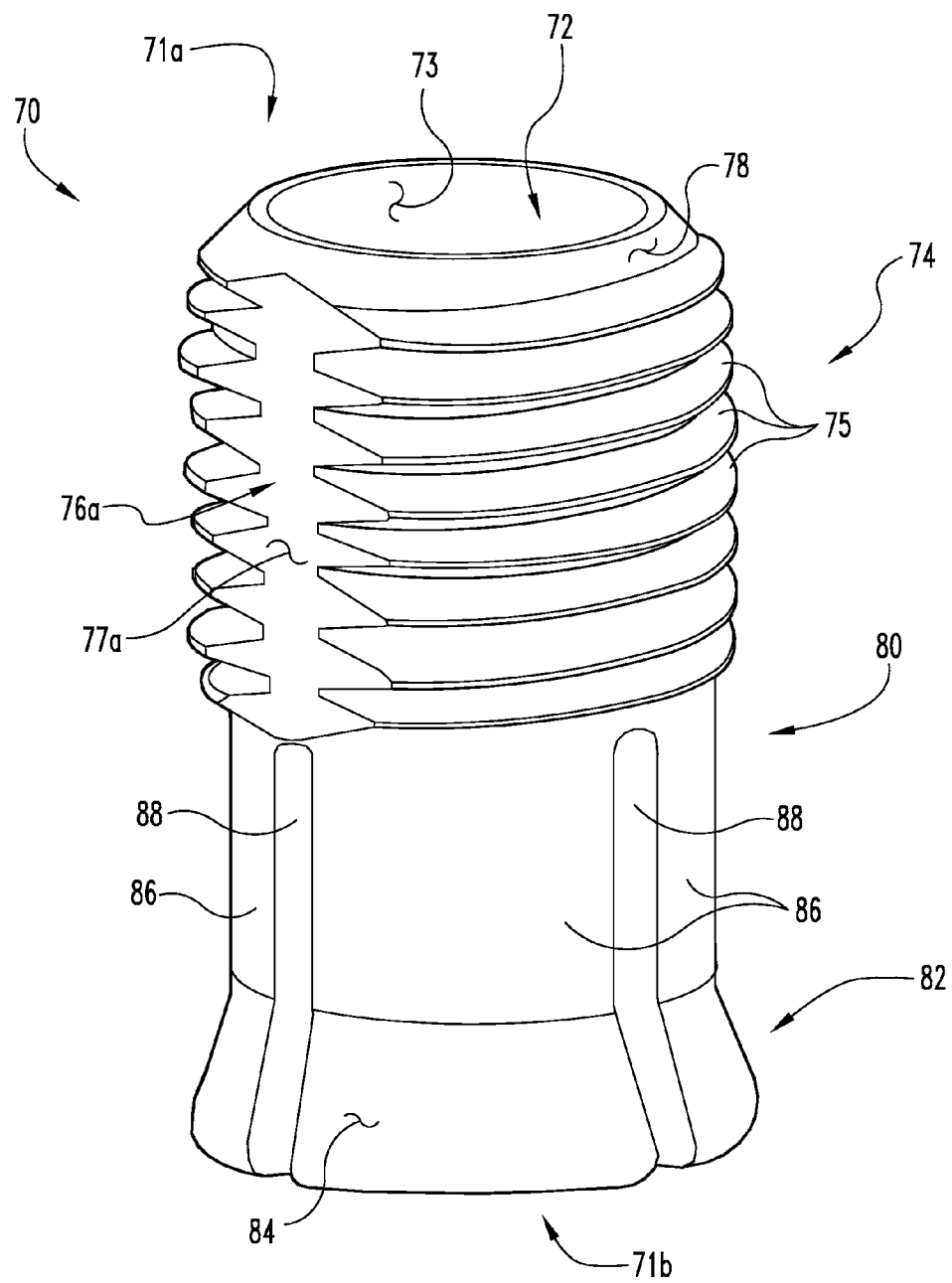
FIG. 6 is a perspective view of a collet member included in the spinal connector assembly illustrated in FIG. 1.

Referring collectively to FIGS. 2 and 6, shown therein are further details associated with the collet member or sleeve 70. In the illustrated embodiment, the collet member 70 has a cylindrical sleeve-like configuration defining generally circular inner and outer cross sections and including an upper side 71a and an oppositely facing lower side 71b. However, other shapes and configurations of the collet member 70 are also contemplated. The collet member 70 defines a passage 72 extending therethrough. In one embodiment, the passage 72 is bound by a substantially circular and smooth inner surface 73 extending from the upper side 71a to the lower side 71b and having a generally uniform inner diameter that corresponds to the substantially circular and smooth outer surface 24 defined by the proximal post portion 22 of the bone screw 14. The collet member 70 includes a threaded upper proximal portion 74 extending from the upper side 71a and defining external threads 75 configured for threading engagement with the internal threads 64 of the ring member 60 and the internal threads 92 of the lock member 90. Additionally, the threaded upper portion 74 defines a pair of truncated regions 76a, 76b positioned generally diametrically opposite one another and extending axially along substantially the entire length of the threaded upper portion 74 so as to circumferentially interrupt the external threads 75. The truncated regions 76a, 76b define generally flat/planar surfaces 77a, 77b that provide the threaded upper portion 74 with a width dimension that is sized slightly smaller than but in relatively close tolerance with the width w of the slotted passage 36 defined in the screw receiving portion 32 of the connector body 30. As shown in FIG. 7, the flat/planar surfaces 77a, 77b of the collet member 70 are proximately engaged with the flat/planar side walls 37a, 37b of the slotted passage 36 to substantially prevent the collet member 70 from rotating relative to the connector body 30 about the axis A. The threaded upper portion 74 may also be provided with a chamfered or conically tapered upper surface 78 adjacent the upper side 71a to facilitate insertion in the screw receiving passage 36 of the connector body 30 and threading engagement with the ring member 60 and the lock member 90.

The collet member 70 further includes a non-threaded central or mid-portion 80 extending axially from the threaded upper portion 74, and a lower distal portion 82 extending axially from the central portion 80 and having an outer cross section sized larger than the outer cross section of the central portion 80. In the illustrated embodiment, the lower distal portion 82 defines an angled or tapered outer surface 84 extending from the central portion 80 to the lower side 71b of the collet member 70. In one embodiment, the tapered outer surface 84 has a conically tapered configuration. However, other shapes and configurations of the outer surface 84 are also contemplated, including a convexly rounded or spherical shaped configuration. As illustrated in FIGS. 7 and 8, the tapered inner surface 66 of the ring member 60 is configured to contact the tapered outer surface 84 defined by the lower portion 82 of the collet member 70 so as to compress or clamp the central portion 80 and the lower portion 82 of the collet member 70 about the proximal post portion 22 of the bone anchor 14 to thereby secure the bone anchor 14 to the collet member 70 and in turn the connector body 30.

In the illustrated embodiment, in order to facilitate inward displacement or collapsing of the central and lower portions 80, 82 of the collet member 70 into clamping engagement about the proximal post portion 22 of the bone anchor 14, the central and lower portions 80, 82 of the collet member 70 are divided into a plurality of movable portions or flexible legs 86 via a corresponding plurality of axially extending slots or slits 88 extending from the lower side 71b of the collet member 70, through the lower portion 82, and at least partially along the central portion 80. The slots 88 may be provided with an enlarged region adjacent the location where the central portion 80 meets the threaded upper portion 74 to minimize stress concentrations and to further facilitate inward displacement or collapsing of the flexible legs 86 into clamping engagement with the proximal post portion 22 of the bone anchor 14. In the illustrated embodiment, the central and lower portions 80, 82 of the collet member 70 are divided into four movable portions or flexible legs 86 via four axially extending slots 88. However, other configurations are also contemplated where the collet member 70 may define any number of movable portions or flexible leg 86. Additionally, in the illustrated embodiment, the inner surfaces 73 of the collet member 70 defining the axial passage 72, including the inner surfaces defined by the flexible legs 86, are substantially smooth. However, in other embodiments, the inner surfaces 73 of the flexible legs 86 and/or the outer surface 24 defined by the proximal post portion 22 of the bone anchor 14 may be roughened or otherwise textured or provided with various types of engagement or interlocking elements to facilitate gripping engagement of the collet member 70 about the proximal post portion 22 of the bone anchor 14.

Referring to FIG. 2, shown therein are further details associated with the lock member 90 and the compression member 100. In the illustrated embodiment, the lock member 90 is configured as a nut including internal threads 92 configured for threading engagement with the external threads 75 formed along the threaded upper portion 74 of the collet member 70. The nut 90 includes a hexagonal-shaped outer surface 94 that is sized and configured for receipt within a hexagonal-shaped socket in a driver instrument such as a wrench (not shown) to facilitate driving of the nut 90 onto the threaded upper portion 74 of the collet member 70 and into compressive engagement with the upper side 31a of the screw receiving portion 32 of the connector body 30. The nut 90 further includes a distal engagement portion 96 defining an angled or conically tapered outer surface 98 configured for abutment against the angled upper surfaces 41a, 41b defined by the screw receiving portion 32 to facilitate secure and stable engagement between the nut 90 and the connector body 30. However, other types and configurations of the nut 90 are also contemplated, including embodiments where the distal end portion of the nut is provided with a concave or convex rounded surface configured for engagement with a correspondingly shaped surface defined by the connector body 30 or an intermediate element, or break-off embodiments where a head portion of the nut may be broken off or otherwise removed from the threaded body portion of the nut subsequent to being driven into engagement with the connector body 30. One example of a break-off nut suitable for use in association with the present invention is illustrated and described in U.S. Patent Application Publication No. 2006/0247624, the contents of which are incorporated herein by reference in their entirety. Additionally, it should be understood that other types and configurations of lock members are also contemplated for use in association with the present invention, including embodiments that are not configured as a nut but which may nevertheless be engaged with the collet member 70 and positioned in compressive engagement with the upper side 31a of the screw receiving portion 32 of the connector body 30.

In the illustrated embodiment, the compression member 100 is configured as a set screw including external threads 102 configured for threading engagement with the internal threads 48 formed along the opening 47 in the rod receiving portion 34 of the connector body 30. In one embodiment, the set screw 100 is provided with a tip 104 to facilitate secure engagement with the elongate rod 16 positioned with the rod receiving passage 46 of the connector body 30. In a further embodiment, the set screw 100 is provided with a hexagonal-shaped tool receiving recess or print 106 that is sized and configured to receive a hexagonal-shaped distal end portion of a driver instrument (not shown) to facilitate driving of the set screw 100 through the opening 47 in the connector body and into engagement with the elongate rod 16. However, other types and configurations of set screws are also contemplated, including break-off type set screws where a head portion of the set screw is broken off or otherwise removed from the threaded body portion subsequent to being driven into engagement with the elongate rod 16. One example of a break-off set screw suitable for use in association with the present invention is illustrated and described in U.S. Pat. No. 6,296,642, the contents of which are incorporated herein by reference in their entirety. Additionally, it should be understood that other types and configurations of compression members are also contemplated for use in association with the present invention, including embodiments that are not configured as a set screw but which may nevertheless be engaged with the connector body 30 and positioned in compressive engagement against the elongate rod 16 positioned with the rod receiving passage 46.

Figure 9C:
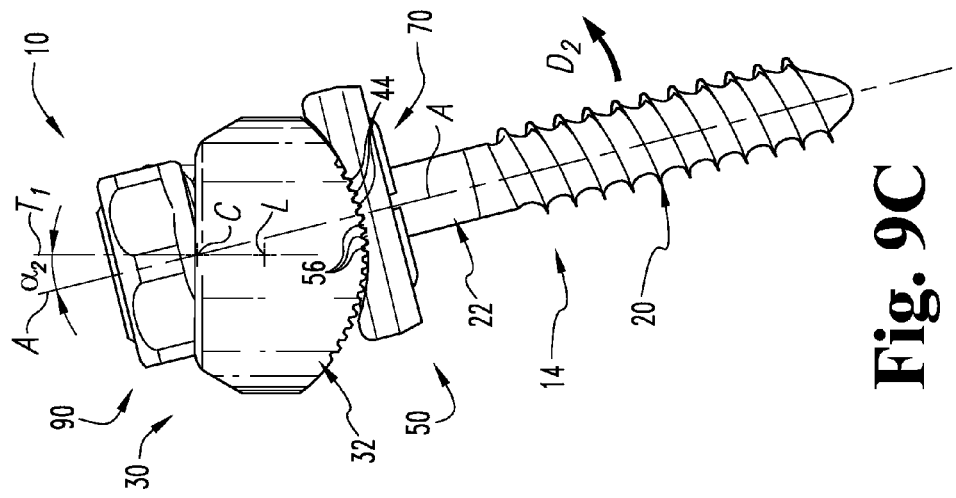
FIG. 9C is an end elevational view of the spinal connector assembly illustrated in FIG. 1, as shown in a third operational position.
Figure 9A:
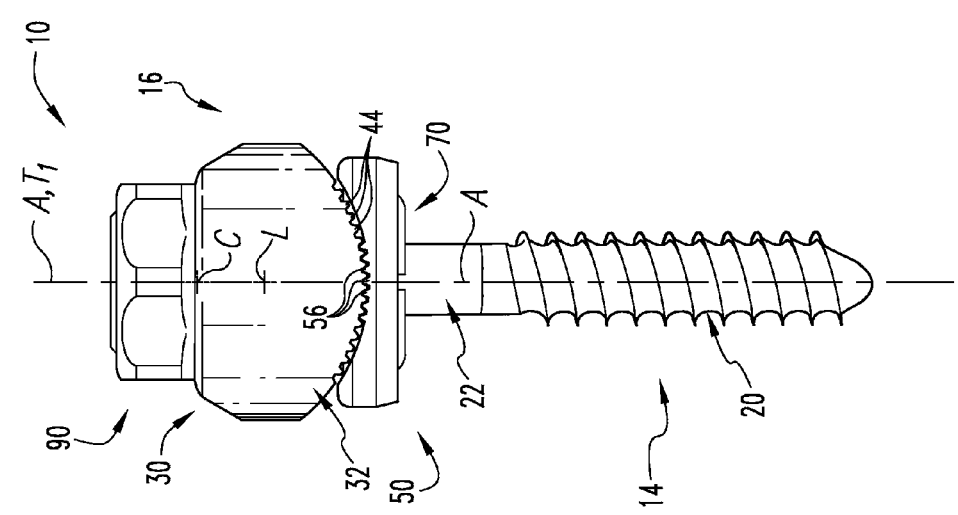
FIG. 9A is an end elevational view of the spinal connector assembly illustrated in FIG. 1, as shown in a first operational position.
Figure 9B:
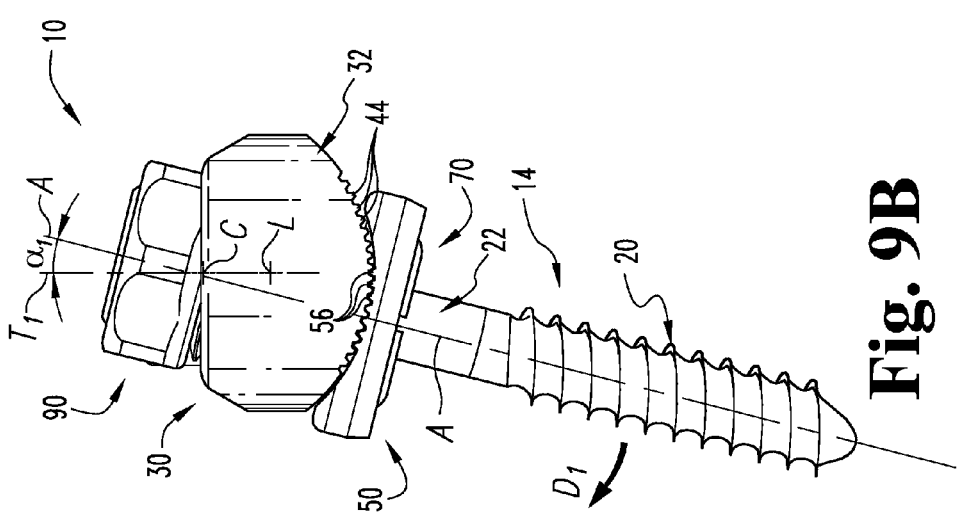
FIG. 9B is an end elevational view of the spinal connector assembly illustrated in FIG. 1, as shown in a second operational position.

Referring to FIGS. 7 and 8, shown therein are cross sectional views taken through the connector assembly 12 which provide further details regarding the relationship and interaction between the components of the connector assembly 12. Additionally, FIGS. 9a-9c show further details regarding the operation and use of the stabilization system 10, including the illustration of three operational positions of the connector assembly 12 which position and selectively lock the bone anchor 14 at various angular orientations relative to the connector body 30 and the elongate support rod 16. Although details regarding the assembly and operation of the stabilization system 10 are set forth below, it should be understood that such details are exemplary and do not in any way limit the scope of the present invention.

The ring member 60 is initially assembled with the collet member 70 by threading the ring member 60 along the threaded upper portion 74 of the collet member 70. Once the ring member 60 is positioned beyond the external threads 75, the ring member 60 can be passed along the central portion 80 of the collet member 70 until the tapered inner surface 66 of the ring member 60 engages and loosely rests against the tapered outer surface 84 defined by the lower portion 82 of the collet member 70. Since the inner cross section of the aperture 62 defined through the ring 60 is smaller than the maximum outer cross section defined by the lower portion 82 of the collet member 70, the ring member 60 is captured and maintained on the collet member 70. The washer member 50 may then be passed over the threaded upper portion 74 and the central portion 80 of the collet member 70 and engaged with the ring member 60 via insertion of the upper portion of the ring member 60 within the lower portion of the opening 52 in the washer member 50 until the inner annular shoulder 53 of the washer 50 abuts the outer annular shoulder 68 of the ring member 60. However, it should be understood that in other embodiments, the washer member 50 may be engaged with the ring member 60 prior to assembly with the collet member 70. Additionally, as discussed above, although the washer member 50 and the ring member 60 are provided as separate pieces, in other embodiments, the washer member 50 and the ring member 60 may be formed integral with one another so as to define a unitary, single-piece structure.

Following the initial assembly of the washer member 50 and the ring member 60 with the collet member 70, the truncated flat surfaces 77a, 77b defined along the threaded upper portion 74 of the collet member 70 are aligned with the flat side walls 37a, 37b of the slotted screw receiving passage 36 in the connector body 30, and the threaded upper portion 74 of the collet member 70 is inserted axially through the slotted passage 36, with the recessed regions 54a, 54b of the washer member 50 arranged generally opposite and generally aligned with the lower protrusions or rails 42a, 42b defined by the screw receiving portion 32 of the connector body 30. As indicted above, the proximate engagement of the flat/planar surfaces 77a, 77b of the collet member 70 with the flat/planar side walls 37a, 37b of the slotted passage 36 prevent the collet member 70 from rotating relative to the connector body 30 about the axis A. The lock member or nut 90 is then loosely threaded onto the threaded upper portion 74 of the collet member 70, thereby provisionally capturing the collet member 70 within the slotted passage 36 of the connector body 30. At this point, the nut 90 is not fully threaded onto the threaded upper portion 74 of the collet member 70 and into engagement with the upper side 33a of the connector body 30. As a result, the collet member 70 is allowed to move freely within the slotted passage 36 including, for example, axial displacement along the transverse axis $T_1$ and/or pivotal or angular displacement within the slotted passage 36 relative to the transverse axis $T_1$. The compression member or set screw 100 can be provisionally threaded into the threading opening 47 in the rod receiving portion 34 of the connector body 30. Alternatively, the set screw 100 can be threaded into the threading opening 47 subsequent to implantation of the connector assembly 12 and/or subsequent to insertion of the elongate rod 16 within the rod receiving passage 46.

In one embodiment, the bone screws 14 are engaged and anchored to respective vertebrae or other bony structures via the threaded shank 20. The spinal rod 16 may then be inserted into the rod receiving passage 46 in the connector body 30, and the connector assembly 12 may be engaged to the proximal post portion 22 of the bone screw 14 via insertion of the proximal post portion 22 into the axial passage 72 of the collet member 70. However, it should be understood that other embodiments are also contemplated where the bone screw 14 and the spinal rod 16 are engaged with the connector assembly 12 in other sequences or assembly steps. For example, in another embodiment, the proximal post portion 22 of the bone screw 14 may be positioned into the axial passage 72 of the collet member 70 prior to anchoring or engagement of the threaded shank 20 with the corresponding vertebra. Additionally, the spinal rod 16 may be inserted into the rod receiving passage 46 in the connector body 30 prior to implantation within the patient, or the spinal rod 16 may be inserted into the rod receiving passage 46 after the connector body 30 is engaged to the bone screw 14. As should be appreciated, the particular assembly sequence can be modified or changed to accommodate various surgical requirements, procedures or preferences.

As set forth above, prior to tightening of the nut 90 into compressed engagement against the upper side 33a of the screw receiving portion 32 of the connector body 30, the collet member 70 is allowed to move freely within the screw receiving passage 36. In this unlocked or loosened state of the connector assembly 12, the collet member 70 is permitted to slide along the length of the proximal post 22 of the bone screw 14 (i.e., along the transverse axis $T_1$) to thereby adjust the dorsal height of the connector body 30 (and the elongate rod 16 positioned with the rod receiving passage 46) relative to the vertebra to which the bone screw 14 is anchored. Furthermore, in the unlocked or loosened state, the collet member 70 and the bone screw 14 positioned within the collet passage 72 are permitted to pivot or angulate within the slotted passage 36 along a plane extending along the length l of the slotted passage 36 (i.e., in a plane parallel with the sagittal plane), thereby allowing the screw axis A to pivot or angulate relative to the vertical transverse axis $T_1$. Such pivotal or angulating movement is also permitted due to the corresponding configurations of the convex curvature of the lower surfaces 43a, 43b defined by the lower protrusions 42a, 42b of the connector body 30 and the concave curvature of the upper surfaces 55a, 55b defined by the recessed regions 54a, 54b of the washer member 50, thereby allowing the washer member 50 to rotate or pivot relative to the connector body 30 about the central axis of rotation C.

Notably, in the unlocked or loosened state of the connector assembly 12, the engagement elements or splines 56 defined along the concave upper surfaces 55a, 55b of the washer member 50 are spaced from and do not matingly engage or interdigitate with the engagement elements or splines 44 defined along the convex lower surfaces 43a, 43b of the connector body 30, thereby allowing the washer member 50 (and the bone screw 14) to freely pivot relative to the connector body 30. It should be further noted that since the washer member 50 is positioned beneath or below the connector body 30 (as opposed to being positioned on top of or above the connector body 30), when the connector assembly 12 is in the unlocked or loosened state, gravitational forces (i.e., the weight of the washer member 50 and the ring member 60) will cause the washer member 50 to drop onto the lower portion 82 of the collet member 70, which will in turn create a gap or spacing between the lower side 33b of the connector body 30 and the upper side 51a of the washer member 50, thereby preventing premature or non-intentional engagement of the splines 56 of the washer member 50 with the splines 44 of the connector body 30 and in turn allowing smooth and uninterrupted pivotal adjustment of the washer member 50 (and the bone screw 14) relative to the connector body 30. In this manner, the splines 56 of the washer member 50 remain spaced and disengaged from the splines 44 of the connector body 30 until the connector assembly 12 is selectively transitioned to a locked or rigid state via tightening of the nut 90. As should be appreciated, this non-engagement or spacing feature would not be apparent if the washer member 50 were located on top of or above the connector body 30, which would otherwise permit premature or non-intentional engagement of the splines of the washer member 50 with the splines of the connector body 30 due to the gravitational forces acting on the washer member 50, which would in turn result in an undesirable skipping or ratcheting sensation when attempting to adjust the angular position of the washer member 50 (and the bone anchor 14) relative to the connector body 30. Accordingly, it should be appreciated that a distinct operational advantage is realized by positioning the washer member 50 beneath or below the screw receiving portion 32 of the connector body 30.

Referring to FIG. 9a, shown therein is an operational configuration of the stabilization system 10 where the axis A of the bone screw 14 is generally aligned and parallel with the vertical transverse axis $T_1$. However, as illustrated in FIGS. 9d and 9c, when the connector assembly 12 is in the unlocked or loosened state, the collet member 70 and the bone screw 14 (as well as the bone screw axis A) are permitted to pivot or angulate within the slotted passage 36 of the connector body 30 along a plane arranged generally parallel with the sagittal plane in the directions of arrows $D_1$ and $D_2$ to maximum pivot angles $\alpha_1$ and $\alpha_2$ relative to the vertical transverse axis $T_1$ of about ±15 degrees. However, it should be understood that the connector assembly 12 may be configured to permit the collet member 70 and the bone screw 14 to pivot or angulate in planes other than the sagittal plane, and/or may be configured to permit maximum pivot angles $\alpha_1$, $\alpha_2$ of greater than or less than ±15 degrees. It should further be understood that the pivot angles $\alpha_1$, $\alpha_2$ need not necessarily be equal to one another, but may instead by non-symmetrical.

Once the dorsal height of the connector body 30 (and the spinal rod 16) and the pivot angle α of the bone screw 14 are appropriately adjusted to their desired position and orientation, the connector assembly 12 is transitioned to a locked or rigid state by tightening the nut 90 along the threaded upper portion 74 of the collet member 70 and into compressed engagement against the upper side 33a of the screw receiving portion 32 of the connector body 30. As shown in FIG. 7, in the illustrated embodiment, the conically tapered outer surface 98 defined by the distal engagement portion 96 of the nut 90 is compressed against the angled upper surfaces 41a, 41b defined by the screw receiving portion 32 of the connector body 30 to facilitate secure and stable engagement between the nut 90 and the connector body 30, regardless of the orientation of the nut 90 relative to the connector body 30. As should be appreciated, tightening of the nut 90 draws the collet member 70 in an upward direction along the slotted passage 36 in the connector body 30, which correspondingly draws the washer member 50 and the ring member 60 in an upward direction, thereby compressing the concave upper surfaces 55a, 55b defined by the recessed regions 54a, 54b in the washer member 50 into compressed engagement with the convex lower surfaces 43a, 43b defined by the lower protrusions 42a, 42b of the connector body 30. Tightening of the nut 90 also causes the engagement elements or splines 56 defined along the concave upper surfaces 55a, 55b of the washer member 50 to matingly engage or interdigitate with the engagement elements or splines 44 defined along the convex lower surfaces 43a, 43b of the connector body 30, thereby preventing further pivotal movement of the washer member 50 relative to the connector body 30, which in turn prevents further pivotal movement of the bone screw 14 relative to the connector body 30.

Additionally, compression of the washer member 50 against the lower side of the connector body 30 forces the inner annular shoulder 53 of the washer member 50 into compressed engagement with the outer annular shoulder 68 of the ring member 60, thereby transferring a downward axial force from the washer member 50 to the ring member 60. The downward axial force applied to the ring member 60 is thereby transferred to the lower portion 82 of the collet member 70 via compressed engagement of the tapered inner surface 66 of the ring member 60 against the tapered outer surface 84 defined by the lower portion 82 of the collet member 70. As should be appreciated, compressed engagement of the tapered inner surface 66 against the tapered outer surface 84 exerts a lateral force component onto the movable portions or flexible legs 86 of the collet member 70, which in turn results in inward displacement or collapsing of the movable portions 86 to force the movable portions 86 into clamped engagement about the proximal post portion 22 of the bone screw 14, thereby preventing further axial movement of the bone screw 14 within the collet member 70 and locking the connector body 30 at a select height/position relative to the bone screw 14.

The set screw 100 can then be tightened into compressed engagement against the spinal rod 16 positioned with the rod receiving passage 46 in the connector body 30, thereby preventing further axial movement of the spinal rod 16 within the passage 46 and locking the spinal rod 16 in position relative to the connector body 30. However, in other embodiments, the spinal rod 16 can be locked in position within the rod receiving passage 46 of the connector body 30 prior to locking the connector body 30 at a select height/position and at a select angular orientation relative to the bone screw 14.

While the invention has been illustrated and described in detail in the drawings and foregoing description, the same is to be considered as illustrative and not restrictive in character, it being understood that only the preferred embodiments have been shown and described and that all changes and modifications that fall within the spirit of the invention are desired to be protected. Additionally, any theory, mechanism of operation, proof or finding stated herein is meant to further enhance understanding of the present invention, and is not intended to make the present invention in any way dependent upon such theory, mechanism of operation, proof or finding.

It should also be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

What is claimed is:

1. A connector assembly for connecting an implant member with an elongate support member, comprising:

a connector body including first and second receiver portions, said first receiver portion defining a first passage extending therethrough from an upper side to an oppositely facing lower side and arranged along a first axis, said second receiver portion defining a second passage extending therethrough and arranged along a second axis transverse to said first axis, said second passage sized to receive a portion of the elongate support member therein;

a collet member defining a third passage extending therethrough and sized to receive a proximal portion of the implant member therein, said collet member extending through said first passage in said connector body and including an upper proximal portion extending axially beyond said upper side of said connector body and a lower distal portion extending axially beyond said lower side of said connector body, said collet member configured to pivot within said first passage of said connector body to position the collet member and the implant member at variable angular orientations relative to said first axis;

a washer member defining an opening extending therethrough and positioned annularly about said lower distal portion of said collet member, said washer member positioned beneath said first receiver portion of said connector body with a top side of said washer member facing said lower side of said first receiver portion, one of said top side and said lower side defining a convex surface, another of said top side and said lower side defining a concave surface facing and generally aligned with said convex surface, wherein said concave surface has a concave curvature substantially corresponding to a convex curvature of said convex surface; and a lock member engaged with said upper proximal portion of said collet member and positioned adjacent said upper side of said first receiver portion of said connector body, said lock member configured to exert an upward force onto said collet member to pull said collet member and said washer member in an upward direction, said upward force drawing said convex and concave surfaces into compressed engagement to thereby lock said washer member and the implant member at a select angular orientation relative to said first receiver portion, said upward force also drawing an outer surface of said collet member against an inner engagement surface to inwardly displace a portion of said collet member into clamped engagement with the proximal portion of the implant member positioned within said third passage to thereby lock said collet member at a select position along the proximal portion of the implant member.

2. The connector assembly of claim 1, wherein said lower side of said first receiver portion of said connector body defines said convex surface and said top side of said washer member defines said concave surface.

3. The connector assembly of claim 1, wherein at least one of said convex surface and said concave surface define engagement elements; and wherein said upward force applied to said lock member draws said engagement elements into engagement with an adjacent surface to facilitate locking of said washer member at said select angular orientation relative to said first receiver portion of said connector body.

4. The connector assembly of claim 3, wherein said convex surface and said concave surface together define a plurality of mating engagement elements that are configured to selectively interdigitate with one another; and wherein said upward force applied to said lock member draws said mating engagement elements into interdigitating engagement with one another to facilitate said locking of said washer member at said select angular orientation relative to said first receiver portion of said connector body.

5. The connector assembly of claim 4, wherein said mating engagement elements comprise a plurality of splines defined along at least a portion of said convex surface that are configured to interdigitate with a plurality of splines defined along at least a portion of said concave surface in response to said upward force to facilitate said locking of said washer member at said select angular orientation relative to said connector body.

6. The connector assembly of claim 3, wherein said engagement elements comprise surface roughening features.

7. The connector assembly of claim 6, wherein said surface roughening features comprise teeth extending across said at least one of said convex and concave surfaces.

8. The connector assembly of claim 7, wherein said convex surface and said concave surface together define a plurality of said teeth configured to selectively intermesh with one another; and wherein said upward force applied to said lock member draws teeth into intermeshing engagement with one another to facilitate said locking of said washer member at said select angular orientation relative to said first receiver portion of said connector body.

9. The connector assembly of claim 1, wherein said lock member comprises a nut defining internal threads that threadingly engage external threads defined along said upper proximal portion of said collet member, said nut tightened into compressed engagement against said upper side of said first receiver portion of said connector body to thereby exert said upward force onto said collet member to pull said collet member and said washer member in said upward direction.

10. The connector assembly of claim 9, wherein said upper side of said first receiver portion defines a pair of angled surfaces arranged on opposite sides of said first passage and tapering inwardly toward said first passage, said nut including a distal engagement portion defining a conically tapered outer surface that is compressed into engagement with said angled surfaces to thereby exert said upward force onto said collet member.

11. The connector assembly of claim 9, wherein said upper proximal portion of said collet member includes a pair of truncated regions defining generally flat surfaces arranged diametrically opposite one another and which extend across and circumferentially interrupt at least a portion of said external threads, said generally flat surfaces interacting with generally flat surface regions defined along said first passage in said connector body to substantially prevent said collet member from rotating within said first passage while permitting said collet member to pivot within said first passage.

12. The connector assembly of claim 1, wherein said collet member includes a plurality of slots extending from a distal end of said collet member toward said upper proximal portion to form a plurality of flexible leg portions, said flexible leg portion flexibly displaced into clamped engagement with the proximal portion of the implant member in response to said upward force to thereby lock said collet member at said select position along the proximal portion of the implant member.

13. The connector assembly of claim 1, wherein said outer surface of said collet member comprises a conical outer surface formed along said lower distal portion.

14. The connector assembly of claim 1, further comprising a ring member defining an aperture extending therethrough, said ring member positioned annularly about said lower distal portion of said collet member adjacent said washer member, said aperture defining said inner engagement surface such that application of said upward force onto said collet member draws said outer surface of said collet member against said inner engagement surface of said ring member to thereby inwardly displace said portion of said collet member into clamped engagement with the proximal portion of the implant member.

15. The connector assembly of claim 14, wherein said inner engagement surface of said ring member and said outer surface of said collet member are both conically shaped.

16. The connector assembly of claim 14, wherein said ring member is at least partially positioned within said opening is said washer member, said ring member engaged with said washer member to transfer an axial force therebetween.

17. The connector assembly of claim 1, wherein said second receiver portion of said connector body includes an opening extending from an outer surface of said connector body and in communication with said second passage; and further comprising a compression member positioned within said opening and compressed into engagement with the elongate support member in said second passage to lock said connector body at a select position along the elongate support member.

18. The connector assembly of claim 1, further comprising an implant member and an elongate support member; and wherein said implant member includes a bone engaging portion and a proximal portion extending from said bone engaging portion, said proximal portion positioned within said third passage of said collet member; and wherein said elongate support member includes a portion positioned within said second passage defined by the said second receiver portion of said connector body.

19. A connector assembly for connecting an implant member with an elongate support member, comprising:
    a connector body including first and second receiver portions, said first receiver portion defining a first passage extending therethrough from an upper side to an oppositely facing lower side and arranged along a first axis, said second receiver portion defining a second passage extending therethrough and arranged along a second axis transverse to said first axis, said second passage sized to receive a portion of the elongate support member therein;
    a collet member defining a third passage extending therethrough and sized to receive a proximal portion of the implant member therein, said collet member extending through said first passage in said connector body and including an upper proximal portion extending axially beyond said upper side of said connector body and a lower distal portion extending axially beyond said lower side of said connector body, said collet member configured to pivot within said first passage of said connector body to position the collet member and the implant member at variable angular orientations relative to said first axis;
    a washer member defining an opening extending therethrough and positioned annularly about said lower distal portion of said collet member, said washer member positioned beneath said first receiver portion of said connector body with a top side of said washer member facing said lower side of said first receiver portion, said top side of said washer member and said lower side of said first receiver portion together defining a plurality of mating engagement elements that are configured to selectively interdigitate with one another; and
    a lock member engaged with said upper proximal portion of said collet member and positioned adjacent said upper side of said first receiver portion of said connector body, said lock member configured to exert an upward force onto said collet member to pull said collet member and said washer member in an upward direction, said upward force drawing said mating engagement elements into interdigitating engagement with one another to thereby lock said washer member and the implant member at a select angular orientation relative to said first receiver portion, said upward force also drawing an outer surface of said collet member against an inner engagement surface to inwardly displace a portion of said collet member into clamped engagement with the proximal portion of the implant member positioned within said third passage to thereby lock said collet member at a select position along the proximal portion of the implant member.

20. The connector assembly of claim 19, wherein said mating engagement elements comprise a first plurality of splines defined along at least a portion of said top side of said washer member and a second plurality of splines defined along at least a portion of said lower side of said first receiver portion, said first plurality of splines configured to interdigitate with said second plurality of splines in response to said upward force to facilitate said locking of said washer member at said select angular orientation relative to said connector body.

21. The connector assembly of claim 19, wherein said mating engagement elements comprise a first plurality of teeth defined along at least a portion of said top side of said washer member and a second plurality of teeth defined along at least a portion of said lower side of said first receiver portion, said first plurality of teeth configured to intermesh with said second plurality of teeth in response to said upward force to facilitate said locking of said washer member at said select angular orientation relative to said connector body.

22. The connector assembly of claim 19, wherein one of said top side of said washer member and said lower side of said first receiver portion defining a convex surface, another of said top side and said lower side defining a concave surface facing and generally aligned with said convex surface; and wherein each of said convex and concave surfaces defines at least one of said engagement elements.

23. The connector assembly of claim 22, wherein said concave surface has a concave curvature substantially corresponding to a convex curvature of said convex surface.

24. A stabilization system configured to stabilize a bony segment, comprising:
an elongate support rod;
a bone anchor including a bone engaging portion and a proximal post portion;
a connector assembly configured to transversely interconnect said elongate support rod with said bone anchor, said connector assembly comprising:
a connector body including first and second receiver portions, said first receiver portion defining a first passage extending therethrough from an upper side to an oppositely facing lower side and arranged along a first axis, said second receiver portion defining a second passage extending therethrough and arranged along a second axis transverse to said first axis, a portion of said elongate support rod positioned within said second passage;
a collet member defining a third passage extending therethrough with said proximal post portion of said bone anchor positioned within said third passage, said collet member extending through said first passage in said connector body and including an upper proximal portion extending axially beyond said upper side of said connector body and a lower distal portion extending axially beyond said lower side of said connector body, said collet member configured to pivot within said first passage of said connector body to position the collet member and said bone anchor at variable angular orientations relative to said first axis;
a washer member defining an opening extending therethrough and positioned annularly about said lower distal portion of said collet member, said washer member positioned beneath said first receiver portion of said connector body with a top side of said washer member facing said lower side of said first receiver portion, one of said top side and said lower side defining a convex surface, another of said top side and said lower side defining a concave surface facing and generally aligned with said convex surface, said convex and concave surfaces together defining a plurality of mating engagement elements that are configured to selectively interdigitate with one another; and
a lock member engaged with said upper proximal portion of said collet member and positioned adjacent said upper side of said first receiver portion of said connector body, said lock member configured to exert an upward force onto said collet member to pull said collet member and said washer member in an upward direction, said upward force drawing said mating engagement elements into interdigitating engagement with one another to thereby lock said washer member and said proximal post portion of said bone anchor at a select angular orientation relative to said first receiver portion, said upward force also drawing an outer surface of said collet member against an inner engagement surface to inwardly displace a portion of said collet member into clamped engagement with said proximal post portion of said bone anchor to thereby lock said collet member at a select position along said proximal post portion of said bone anchor.

25. The system of claim 24, wherein said concave surface has a concave curvature substantially corresponding to a convex curvature of said convex surface.

26. The system of claim 24, wherein said mating engagement elements comprise a plurality of splines defined along at least a portion of said convex surface that are configured to interdigitate with a plurality of splines defined along at least a portion of said concave surface in response to said upward force to facilitate said locking of said washer member at said select angular orientation relative to said connector body.

27. The system of claim 24, wherein said lock member comprises a nut defining internal threads that threadingly engage external threads defined along said upper proximal portion of said collet member, said nut tightened into compressed engagement against said upper side of said first receiver portion of said connector body to thereby exert said upward force onto said collet member to pull said collet member and said washer member in said upward direction.

28. The system of claim 24, further comprising a ring member defining an aperture extending therethrough, said ring member positioned annularly about said lower distal portion of said collet member adjacent said washer member, said aperture defining said inner engagement surface such that application of said upward force onto said collet member draws said outer surface of said collet member against said inner engagement surface of said ring member to thereby inwardly displace said portion of said collet member into clamped engagement with the proximal portion of the implant member.

29. The system of claim 24, wherein said second receiver portion of said connector body includes an opening extending from an outer surface of said connector body and in communication with said second passage; and further comprising a compression member positioned within said opening and compressed into engagement with said portion of said elongate support rod positioned within said second passage to lock said connector body at a select position along said elongate support rod.

* * * * *